United States Patent [19]

Moore et al.

[11] Patent Number: 5,693,308
[45] Date of Patent: Dec. 2, 1997

[54] MAGNETIC RESONANCE BLOOD POOL AGENTS BOUND TO HUMAN SERUM ALBUMIN

[75] Inventors: Dennis A. Moore, Ferguson; Stephen R. Cooper, St. Louis; Rebecca Abernathy Wallace, Manchester; Michael R. Hynes, Florissant, all of Mo.

[73] Assignee: Mallinckrodt Medical, Inc., St. Louis, Mo.

[21] Appl. No.: 604,286

[22] Filed: Feb. 21, 1996

[51] Int. Cl.[6] ............... A61K 49/00; G01N 31/00; G01N 33/48
[52] U.S. Cl. ............... 424/9.34; 424/9.1; 424/9.3
[58] Field of Search ............... 424/1.11, 1.65, 424/1.69, 9.1, 9.3, 9.34, 9.4, 9.42, 9.5; 534/10–16; 436/88; 530/300, 362, 636

[56] References Cited

U.S. PATENT DOCUMENTS

| | | | |
|---|---|---|---|
| 4,559,221 | 12/1985 | Arano et al. | 424/1.11 |
| 4,647,447 | 3/1987 | Gries et al. | 424/9 |
| 4,746,505 | 5/1988 | Jones et al. | 424/1.11 |
| 5,095,111 | 3/1992 | Lever et al. | 540/544 |
| 5,138,040 | 8/1992 | Moore et al. | 534/16 |
| 5,196,515 | 3/1993 | Lever et al. | 530/300 |
| 5,310,536 | 5/1994 | Srinivasan | 424/1.65 |
| 5,393,512 | 2/1995 | Vanderheyden et al. | 424/1.69 |
| 5,401,489 | 3/1995 | Born et al. | 424/1.11 |
| 5,443,815 | 8/1995 | Dean et al. | 424/1.69 |

FOREIGN PATENT DOCUMENTS 9408630 4/1994 WIPO.

OTHER PUBLICATIONS

Verbeke et al (1993), European J. of Nuclear Medicine, vol. 20, No. 6, pp. 473–482, "Technetium–99m mercapto albumin as a potential substitute for technetium–99 m labeled red blood cells".

Moore et al (1977), Journal of Labelled Compounds and Radiopharmaceuticals, vol. 13, No. 4, pp. 539–550, "Indium Labeled Particles for Lung Imaging: Homogenous and Heterogeneous phase reactions".

Jenkins (1991), Life Science, vol. 48, pp. 1227–1240, "Detection of Site–Specific binding and co–binding, of Ligands to Macromolecules Using 19FNMR".

*Primary Examiner*—John Kight
*Assistant Examiner*—Dameron Jones
*Attorney, Agent, or Firm*—Brian K. Stierwalt

[57] ABSTRACT

The present invention provides compositions comprising a contrast agent capable of reversibly binding to thiol groups of blood-borne proteins. The compositions of the invention provide increased residence time of the contrast agent in the vasculature, thus providing effective blood pool contrast agents. The invention also provides methods for imaging a patient comprising administering a composition of the invention and obtaining an image.

18 Claims, No Drawings

MAGNETIC RESONANCE BLOOD POOL AGENTS BOUND TO HUMAN SERUM ALBUMIN

FIELD OF THE INVENTION

The invention is in the field of imaging. Particularly, the invention is in the magnetic resonance imaging (MRI) field. And most particularly, the invention is in the field of MRI of the blood pool.

BACKGROUND OF THE INVENTION

The use of contrast agents in diagnostic medicine is rapidly growing. In conventional proton magnetic resonance imaging (MRI) diagnostics, increased contrast of internal organs and tissues may be obtained by administering compositions containing paramagnetic metal species which increase the relaxivity of water protons surrounding the tissue.

The technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, in organs and tissues. The technique of MRI is advantageously non-invasive as it avoids the use of ionizing radiation.

While the phenomenon of NMR was discovered in 1945, its potential use as MRI agent to map the internal structure of the body was originally suggested by Lauterbur in 1973. (*Nature*, 242. 190–191 [1973]). The fundamental lack of any known hazard associated with the level of the magnetic field and radio-frequency wave that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium withthe magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal.

By reason of its sensitivity to subtle physico-chemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

Typically, paramagnetic ions have been administered in the form of complexes with organic complexing agents. Such complexes provide the paramagnetic ions in a soluble, non-toxic forms, and facilitate their rapid clearance from the body following the imaging procedure. Gries, et al., U.S. Pat. No. 4,647,447, disclose complexes of various paramagnetic ions with conventional aminocarboxylic acid complexing agents. A preferred complex disclosed by Gries, et al. is the complex of gadolinium (III) with diethylenetriaminepentaacetic acid ("DTPA").

With acceptance and widespread use of MRI, new needs for contrast agents arise. Historically, in the field of MR contrast agent development, efforts to produce such agents have primarily focused upon derivatizing polymers with relaxation agents (e.g. Gd-DTPA polylsine) as well as polyethylene glycol-or carbohydrate-coated paramagnetic or supermagnetic particles. Such agents have not found widespread use because they remain indefinitely in the vasculature or present significant physiological side effects. Clinicians have repeatedly expressed their desire for contrast agents that remain concentrated in the blood, versus surrounding tissue, for extended periods of time.

SUMMARY OF THE INVENTION

The present invention provides compositions comprising a contrast agent capable of reversibly binding to thiol groups of blood-borne proteins. The compositions of the invention provide increased residence time of the contrast agent in the vasculature, thus providing effective blood pool contrast agents. The invention also provides methods for imaging a patient comprising administering a composition of the invention and obtaining an image.

DETAILED DESCRIPTION OF INVENTION

Any thiol or disulfide capable of reacting with a disulfide or thiol of a blood-borne protein can be used with the desired contrast agent. The thiol or disulfide to thiol or disulfide linkage could be effected either in vivo, by injecting the thiol or disulfide containing contrast agent, or alternatively, in vitro, by reaction of a blood-borne protein with the thiol or disulfide bearing the contrast agent followed by injection of the resulting derivatized protein.

Examples of contrast agents incorporating a disulfide moiety is depicted in the following schematics:

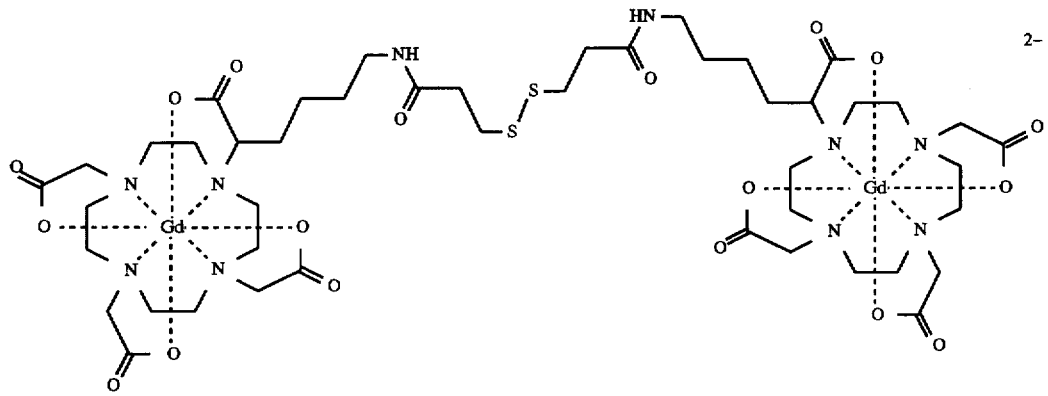

Prototypical macrocyclic Gd complex incorporating the disulfide moiety.

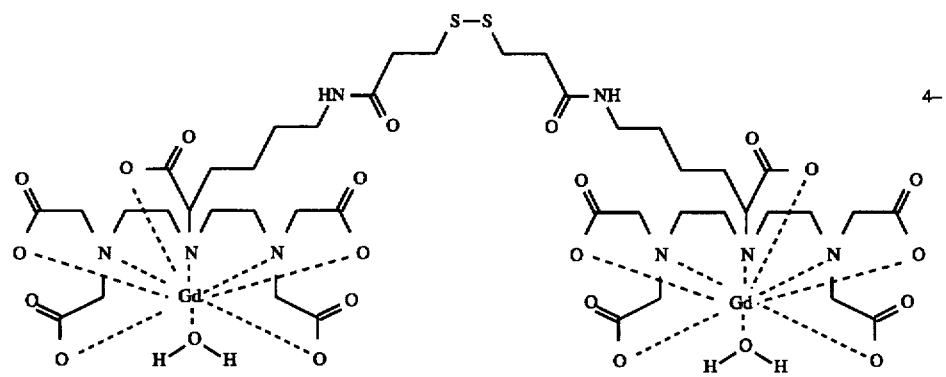

Prototypical Gd complex incorporating the disulfide moiety.

Suitable moieties containing thiols for use with the invention include mercaptoacetyl, 2-mercaptoaminoethyl, mercaptobenzoyl, 3-mercaptopropionyl and thiosalicyl. Suitable disulfides containing moieties for use with the invention include dithiodiacetyl, dithiodiacetocarbamoyl, 2,2'-dithiodiaminoethyl, dithiodibenzoyl, 3,3'-dithiodiproprionyl and dithiodisalicyl. Thiols and disulfides for use with the invention are typically readily available from sources such as Aldrich (Milwaukee, Wisconsin). An article by J. P. Mahieu et al., Int. J. Biol. Macromol., 1993, Vol. 15, pp 233–240, incorporated herein by reference, provides numerous disulfide and thiol moieties one can use with the invention.

Human serum album (HSA), the most prevalent protein in plasma, has 17 disulfide linkages and one free thiol group in a single-chain 69 kD protein. (see He, X. M.; Carter, D. C. Nature 1992, 358, 209) Disulfides and free thiols such as those in HSA undergo an exchange reaction to give a new disulfide and free thiol (i.e., RSSR+RSH=RSSR+RSH, the disulfide exchange reaction). Indeed, it has been shown that cysteine is liberated from isolated HSA upon standing; (see King, T. P. J. of Biol. Chem. 1961, 236, 5 & Janatova, J; Fuller, J. K.; Hunter, M. J. J. of Biol. Chem. 1968, 243, 3612). The source of cysteine is a mixed disulfide, HSA-cysteine, which forms from HSA (thiol) and dissolved cystine (cys-S-S-cys) present in the blood plasma. This demonstrates that not only can HSA form a mixed disulfide, but also that a mixed disulfide-HSA species undergoes spontaneous bond fission, in the presence of other thiols, to liberate one of the starting thiols. The disulfide exchange reaction is not restricted to cystine and HSA. It has been demonstrated that small molecule disulfides enter into the disulfide exchange reaction with HSA (see Mahieu, J. P.; Gosslet, N. M.; Sebille, B.; Garel, M. C.; Beuzard, Y. Int. J. Biol. Macromol. 1993, 15, 233 & Kuwata, K.; Era, S.; Sogami, M. Biochim. Biophys. 1994, 1205, 317). A particular thiol binding site on HSA is cysteine-34. The Gd-L-S-S-HSA reaction can take place in vivo or in vitro.

The following schematics depict disulfide exchange reactions of the invention:

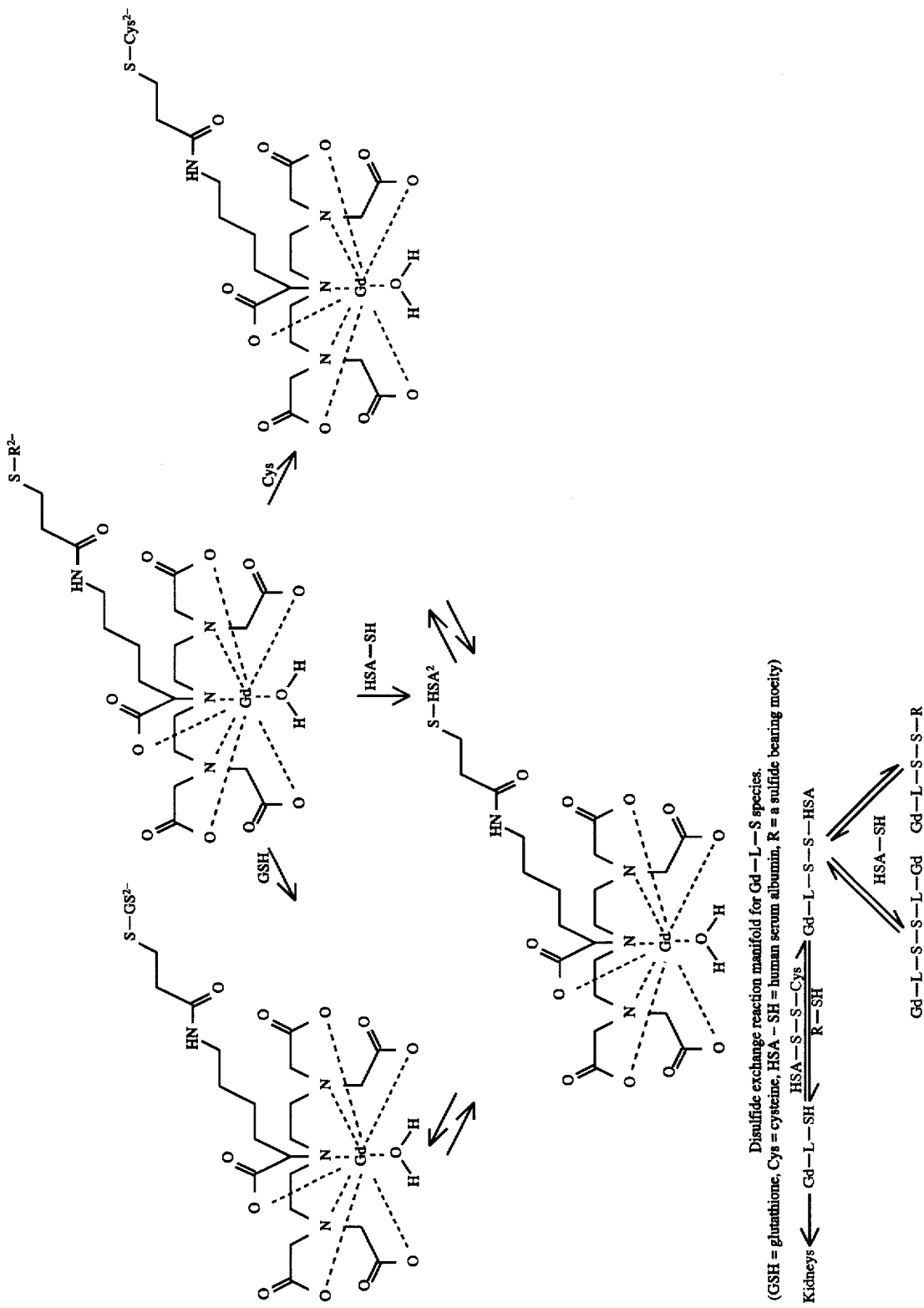

Three approaches to exploit the disulfide exchange mechanism with HSA's. Dimeric disulfide complexes and mixed disulfide complexes can react directly with HSA-SH in the plasma to produce the high relaxivity contrast agent, Gd-L-S-S-HSA, in vivo. Thiol-Gd complexes can undergo exchange with mixed HSA-disulfides to produce the active contrast agent. The complex may be eliminated as a low molecular weight thiol, or disulfide, by the reaction of Gd-L-S-S-HSA with endogenous thiols, R-SH.

It is believed the invention aids in retarding glomerular filtration of the lower-molecular contrast agents. Also, due to the reversible binding of the contrast agent to the bloodborne protein, the contrast agent can be released back into the bloodstream and eliminated by renal excretion.

In general, paramagnetic species such as ions of elements with atomic numbers of 22 to 29, 42 to 44 and 58 to 70 have been found effective as MRI image contrasting agents. Examples of suitable ions include chromium (III), manganese (II), manganese (III), iron (II), iron (III), cobalt (II), nickel (II), copper (II), praseodymium (III), neodymium (III), samarium (III), and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

The compositions of the invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging procedure, the NMR imaging equipment being used, and the like. In general, parenteral dosages will range from about 0.001 to about 1.0 MMol of paramagnetic ion complex per kg of patient body weight. Preferred parenteral dosages range from about 0.01 to about 0.5MMol of paramagnetic ion complex per kg of patient body weight.

Enteral dosages generally range from about 0.5 to about 100 MMol, preferably from about 1.0 to about 10 MMol, preferably from about 1.0 to about 20.0 MMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the NMR imaging procedure. Protocols for imaging and instrument procedures are found in texts such as Stark, D. D.; Bradley, W. G. Magnetic Resonance Imaging; Mosby Year Book: St. Louis, Mo., 1992.

The following examples illustrate the specific embodiments of the invention described in this document. As would be apparent to skilled artisans, various changes and modifications are possible and are contemplated within the scope of the invention described.

EXAMPLES

Example I

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A diagnostic composition comprising a contrast agent containing a thiol or disulfide through which it is reversibly bound to a thiol or disulfide moiety of human serum albumin.

2. The diagnostic composition of claim 1 wherein the thiol moiety on the contrast agent is selected from mercaptoacetyl, 2-mercaptoaminoethyl, mercaptobenzoyl, 3-mercaptopropionyl and thiosalicyl.

3. The composition of claim 1 wherein the thiol moiety is mercaptoacetyl.

4. The composition of claim 1 wherein the thiol moiety is 2-mercaptoaminoethyl.

5. The composition of claim 1 wherein the thiol moiety is 3 thiosalicyl.

6. The composition of claim 1 wherein the disulfide moiety on the contrast agent is selected from dithiodiacetyl, dithiodiacetacarbamoyl, 2,2'-dithiodiaminoethyl, dithiodibenzoyl, 3,3'-dithiodiproprionyl and dithiodisalicyl.

7. The composition of claim 6 wherein the disulfide moiety is dithiodiacetyl.

8. The composition of claim 6 wherein the disulfide moiety is dithiodibenzoyl.

9. The composition of claim 6 wherein the disulfide moiety is 3,3'-dithiodiproprionyl.

10. A method of imaging a patient comprising the administration of a diagnostically effective amount of a composition comprising a contrast agent containing a thiol or disulfide reversibly bound to a thiol or disulfide moiety of human serum albumin, and obtaining an image.

11. The method of claim 10 wherein the disulfide on the contrast agent is selected from dithiodiacetyl, dithiodiacetacarbamoyl, 2,2'-dithiodiaminoethyl, dithiodibenzoyl, 3,3'-dithiodiproprionyl and dithiodisalicyl.

12. The method of claim 11 wherein the disulfide moiety is dithiidoacetyl.

13. The method of claim 11 wherein the disulfide moiety is dithiodibenzoyl.

14. The method of claim 11 wherein the disulfide moiety is 3,3'-dithiodiproprionyl.

15. The method of claim 10 wherein the thiol moiety on the contrast agent is selected from mercaptoacetyl, 2-mercaptoaminoethyl, mercaptobenzoyl, 3-mercaptopropionyl and thiosalicyl.

16. The method of claim 15 wherein the thiol moiety is mercaptoacetyl.

17. The method of claim 15 wherein the thiol moiety is 2-mercaptoaminoethyl.

18. The method of claim 15 wherein the thiol moiety is thiosalicyl.

* * * * *